United States Patent [19]

Hofmann et al.

[11] Patent Number: 5,049,583
[45] Date of Patent: Sep. 17, 1991

[54] NOREMOPAMIL, AND ITS USE FOR TREATING HYPOXIC CONDITIONS

[75] Inventors: Hans P. Hofmann, Limburgerhof; Werner Seitz, Plankstadt; Hans-Joerg Treiber, Bruehl, all of Fed. Rep. of Germany

[73] Assignee: BASF Aktiengesellschaft, Ludwigshafen, Fed. Rep. of Germany

[21] Appl. No.: 311,780

[22] Filed: Feb. 17, 1989

[30] Foreign Application Priority Data

Feb. 19, 1988 [DE] Fed. Rep. of Germany ....... 3805225

[51] Int. Cl.$^5$ .................. A61K 31/275; C07C 119/00
[52] U.S. Cl. ..................................... 514/523; 558/408
[58] Field of Search ........................ 558/408; 514/523

[56] References Cited

FOREIGN PATENT DOCUMENTS 0147707  7/1986  European Pat. Off. ............ 558/408
3143356  5/1983  Fed. Rep. of Germany ...... 558/408

OTHER PUBLICATIONS

Weber et al., Chem. Abstracts, vol. 109(3) 16607h (1988).
Seitz et al., Chem. Abstracts, vol. 99(11) 87800b (1983).
Chemical Abstracts, Eleventh Collective Index, vols. 96–105, 1982–196, p. 16, col. 3, lines 40–42.
Chemical Abstracts, vol. 109, No. 3, Jul. 18, 1988, p. 17, col. 2, Abstract No. 16607h.
Chemical Abstracts, vol. 99, 1983, p. 542, (11) 87900j.

Primary Examiner—Johann Richter
Attorney, Agent, or Firm—Oblon, Spivak, McClelland, Maier & Neustadt

[57] ABSTRACT

Noremopamil and its preparation are described. The substance is suitable for the treatment of disorders.

6 Claims, No Drawings

NOREMOPAMIL, AND ITS USE FOR TREATING HYPOXIC CONDITIONS

The present invention relates to racemic noremopamil (=2-isopropyl-5-phenethylamino-2-phenylvaleronitrile) and its (S)-enantiomer and their use.

Racemic noremopamil has erroneously been given the Registry Number 86656-29-3 by Chemical Abstracts, although this compound appears neither in the corresponding Chemical Abstracts abstract (CA 99 (11), 87900 b (1983)) nor in the related patent application (German Laid-Open Application DOS 3,143,356).

European Laid-Open Application 147,707 describes 2-isopropyl-5-(methylphenethylamino)-2-phenyl-valeronitrile (referred to below as emopamil) and its enantiomers and their use in the treatment of disorders, including hypoxic conditions of the brain.

We have found that racemic noremopamil and its (S)-enantiomer and their salts with physiologically tolerated acids are substantially superior to emopamil and its enantiomers in the protective treatment of hypoxic tissue damage.

Noremopamil can be prepared by the processes described in European Laid-Open Application 231,003. The reaction of α-isopropylbenzyl cyanide with N-(3-chloropropyl)-phenethylamine under phase transfer catalysis is preferred.

The (S) enantiomer is obtained by reacting the racemate with a chiral acid, separating the resulting mixture of the diastereomeric salts, liberating the base from the pure diastereomeric salt and, if necessary, converting the base into its salts with physiologically tolerated acids.

Examples of chiral acids are the optically active forms of camphor-10-sulfonic acid, camphoric acid, tartaric acid, mandelic acid and O,O'-diacetyl-, O,O'-dibenzoyl- and O,O'-di-p-toluoyltartaric acid.

The diasteromeric salts can be separated in a conventional manner, for example by fractional crystallization or column chromatography.

Resolution of the racemate can also be effected chromatographically over chiral carriers. For example, β-cyclodextrin, cellulose esters (acetates, benzoates or cinnamates), cellulose phenylcarbamates, cellulose tribenzyl ethers, orosomucoid bound to silica gel and optically active polymethyl acrylates are suitable for this purpose. In this case, the (S)-enantiomer is obtained directly by passing the racemate through a column of the stated carriers.

(S)-noremopamil is also obtained by reacting (S)-emopamil with a chloroformate to give the carbamate, which is converted into (S)-noremopamil in a known manner (T. W. Greene, Protective Groups in Organic Synthesis, J. Wiley, New York 1981, page 223).

Sulfuric acid, phosphoric acid, tartaric acid, acetic acid, lactic acid, maleic acid, fumaric acid and in particular hydrochloric acid are specific examples of physiologically tolerated salts which are suitable for salt formation with noremopamil and its (S)-enantiomer.

As mentioned above, noremopamil and its (S)-enantiomer are very suitable for the protective treatment of hypoxic conditions of vital organs, in particular of the brain.

The substantial superiority of noremopamil and its (S)-enantiomer could be demonstrated on the model of normobaric hypoxia:

Female albino mice (NMRI, Ivanovas, Kisslegg; weight: 22–28 g), sitting individually in glass tubes, in a flow-through apparatus, are exposed to a gas mixture of 3.5% of $O_2$ and 96.5% of $N_2$, which is passed in via a rotameter at a flow rate of 4 l/min. 1 hour after peroral pretreatment, the survival time of the animals is determined, this being the time from the beginning of gas flow to the cessation of respiration. Among 6 animals tested simultaneously there is always 1 control animal.

The dose in mg/kg (at 95% confidence level) which prolongs the survival time of the treated animals compared with the control group by 33% is determined, as the $ED_{33\%}$, by means of linear regression from the survival times, based on placebo-treated control animals, of animals treated with the substance and the logarithmic doses (mg/kg).

Table 1 shows that noremopamil and its (S)-enantiomer have a substantially superior cerebral protective action compared with emopamil and its (S)-enantiomer.

TABLE 1

| Comparison of the cerebral protective action | |
|---|---|
| Prolongation of the survival time under normobaric hypoxic hypoxia (3.5% $O_2$ and 96.5% $N_2$) 1 hour after peroral pretreatment in the mouse; $ED_{33\%}$ is the dose which prolongs the survival time by 33% in comparison with placebo-treated control animals. | |
| Substance | $ED_{33\%}$ mg/kg p.o. |
| Noremopamil | 10.3 |
| (S)-noremopamil | 4.2 |
| Emopamil | 51.1 |
| (S)-emopamil | 32.1 |

Noremopamil and its (S) enantiomer are particularly suitable for the treatment of acute and chronic hypoxid conditions of vital organs, especially the brain. These acute hypoxic or ischemic conditions which occur, for example, as a result of cerebral infarction, craniocerebral trauma or vascular spasms and as a result of cardiovascular failure, for example in the case of cardiac arrest, cardiac arrhythmias or cardiovascular shock. Examples of clinical pictures with chronic hypoxic conditions are transitory ischemic attack (TIAs) and prolonged reversible ischemic neurological deficits (PRINDs), as well as multiinfarction dementia and arteriosclerotic psychosis and migraines of vascular origin.

Noremopamil and its (S)-enantiomer can be administered in a conventional manner orally or parenterally (intravenously, intramuscularly or intraperitoneally).

The dose depends on the age, condition and weight of the patient and on the route of administration. As a rule, the daily dose of active compound is about 1–50 mg/kg body weight in the case of oral administration and about 0.1–5 mg/kg body weight in the case of parenteral administration.

Noremopamil and its (S)-enantiomer can be used in the conventional solid or liquid pharmaceutical forms, for example as tablets, film tablets, capsules, powders, granules, coated tablets or solutions. These are prepared in the conventional manner, and to do so the active compounds are mixed with the conventional pharmaceutical auxiliaries, such as tablet binders, fillers, preservatives, tablet disintegrants, flow regulators, plasticizers, wetting agents, dispersants, emulsifiers, solvents, retarding agents and/or antioxidants (cf. H. Sucker et al: Pharmazeutische Technologie, Thieme-Verlag, Stuttgart, 1978). The administration forms thus obtained normally contain the active compound in an amount of from 1 to 99 percent by weight.

The examples which follow illustrate the invention.

EXAMPLE 1

2-Isopropyl-5-phenethylamino-2-phenylvaleronitrile 15.9 g (0.1 mol) of α-isopropylbenzyl cyanide were dissolved in 20 ml of toluene in a three-necked flask equipped with a stirrer, a dropping funnel and a reflux condenser. 32.5 g of 85% strength technical grade potassium hydroxide powder and 0.2 g of tris-(3,6-dioxaheptyl)amine were added to the solution. The vigorously stirred reaction mixture was heated to 80° C. and, beginning at this temperature, a solution of 19.8 g (0.1 mol) of N-(3-chloropropyl)phenethylamine in 20 ml of toluene was added dropwise at a rate such that the reaction temperature did not exceed 85° C. After the end of the addition, stirring was continued for 3 hours at 85°-90° C.

100 ml of water and 100 ml of toluene were added to the cold reaction mixture. The toluene phase was separated off, washed several times with water and dried, and the solvent was stripped off to give 30 g of an oily residue, which was dissolved in 200 ml of ethyl acetate. Ethanolic hydrochloric acid was then added and the mixture was left to stand overnight, after which 32 g (92%) of the hydrochloride of melting 163°-164° C. were isolated.

EXAMPLE 2

(S)-2-Isopropyl-5-phenethylamino-2-phenylvaleronitrile 38.4 g (0.12 mol) of racemic 2-isopropyl-5-phenethylamino-2-phenylvaleronitrile and 48.5 g (0.12 mol) of (+)-O,O'-di-4-toluoyl-D-tartaric acid were dissolved in 400 ml of isopropanol with heating. The crystals which were precipitated overnight were filtered off under suction and recrystallized twice from a 3:1 ethanol/water mixture. The measured optical rotation $[\alpha]_{589}^{20}$ of +46.0 (methanol, c=10 mg/ml) did not change as a result of repeating the crystallization. The base liberated from the salt was dissolved in 100 ml of ethyl acetate, and ethanolic hydrochloric acid was added until the pH was 3. Filtration under suction and drying gave 12.8 g of the hydrochloride of melting point 178°-180° C., $[\alpha]_{589}^{20}$ = −10.2 (ethanol, c=10 mg/ml).

EXAMPLE 3

(S)-2-Isopropyl-5-phenethylamino-2-phenylvaleronitrile

A solution of 17 g (50 mmol) of (S)-2-isopropyl-5-(methylphenethylamino)-2-phenylvaleronitrile in 50 ml of dichloromethane was added dropwise, at 0° C., to a solution of 6 ml (66 mmol) of vinyl chloroformate in 30 ml of dichloromethane. The temperature was then allowed to increase to room temperature, and the mixture was heated for 1 hour at 80° C.

The solvent was distilled off, after which the residue was taken up in 100 ml of n-hexane and the solution was extracted with 0.5% strength aqueous amidosulfonic acid. The organic phase was washed with dilute potassium carbonate solution, dried over sodium sulfate, after which the solvent was distilled off and the residue was taken up in 100 ml of dry dichloromethane. The solution was saturated with hydrogen chloride at 0° C. and then left to stand at room temperature for 4 hours. The solvent was distilled off, after which the residue was taken up in 150 ml of methanol and the solution was heated at 50° C. for 30 minutes. The methanol was distilled off and 30 ml of water were added to the residue. 8 g of the hydrochloride of melting point 178°-180° C., $[\alpha]$ = −10.2 (ethanol, c=10 mg/ml), crystallized out.

EXAMPLE 4

Tablets having the following composition are pressed on a tabletting press in a conventional manner:
40 mg of the substance of Example 1
120 mg of corn starch
13.5 mg of gelatin
45 mg of lactose
2.25 mg of Aerosil ® (chemically pure submicroscopic silica)
6.75 mg of potato starch (as a 6% strength paste).

EXAMPLE 5

Coated tablets having the following composition were prepared in the conventional manner:
20 mg of the substance of Example 2
60 mg of core material
60 mg of sugar-coating material.

The core material consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consists of 5 parts of sucrose, 2 parts of corn starch, 2 parts of calcium carbonate and 1 part of talc. The coated tablets thus prepared are then provided with a coating which is resistant to gastric juice.

EXAMPLE 6

10 g of the substance of Example 3 are dissolved in 5,000 ml of water with the addition of NaCl and the solution is brought to pH 6.0 with 0.1N NaOH, so that a blood-isotonic solution is formed. 5 ml portions of this solution are introduced into ampoules and sterilized.

We claim:
1. (S)-2-isopropyl-5-phenethylamino-2-phenylvaleronitrile or a pharmaceutically acceptable salt thereof.
2. The pharmaceutically-acceptable salt of claim 1, which is a salt of sulfuric acid, phosphoric acid, tartaric acid, acetic acid, lactic acid, maleic acid, fumaric acid and hydrochloric acid.
3. A method of treating hypoxic conditions in a patient suffering therefrom, which comprises administering to said patient an effective amount of the compound or salt thereof as claimed in claim 1.
4. The method according to claim 3, wherein about 1-50 mg/kg of body weight is used for oral administration and about 0.1-5 mg/kg of body weight is used for parenteral administration.
5. A method of protecting a mammal from the effects of hypoxic conditions, which comprises administering to said mammal an effective amount of the compound or salt thereof of claim 1, prior to exposure of said mammal to said conditions.
6. The method according to claim 5, wherein said mammal is a human.

* * * * *